US008688621B2

(12) United States Patent
Mustafa (10) Patent No.: US 8,688,621 B2
(45) Date of Patent: Apr. 1, 2014

(54) SYSTEMS AND METHODS FOR INFORMATION COMPRESSION (75) Inventor: Shakeel Mustafa, Fremont, CA (US)

(73) Assignee: NetCee Systems, Inc.

( * ) Notice: Subject to any disclaimer, the term of this patent is extended or adjusted under 35 U.S.C. 154(b) by 1263 days.

(21) Appl. No.: 12/425,920

(22) Filed: Apr. 17, 2009

(65) Prior Publication Data
US 2009/0204626 A1 Aug. 13, 2009

Related U.S. Application Data (63) Continuation-in-part of application No. 12/183,722, filed on Jul. 31, 2008.

(60) Provisional application No. 61/054,632, filed on May 20, 2008.

(51) Int. Cl.
H03M 7/00 (2006.01)

(52) U.S. Cl.
USPC ............................ 707/101; 382/253; 380/269

(58) Field of Classification Search
USPC ............................................................ 707/1
See application file for complete search history.

(56) References Cited

U.S. PATENT DOCUMENTS 5,392,212 A * 2/1995 Geist .............................. 715/236
5,982,439 A * 11/1999 Parke ........................ 375/240.16
6,101,276 A * 8/2000 Adiletta et al. ............... 382/236
6,826,626 B1 * 11/2004 McManus ..................... 709/246
7,403,136 B2 * 7/2008 De La Cruz et al. ............ 341/51
7,869,989 B1 * 1/2011 Harvey et al. ...................... 704/9
2001/0019628 A1 * 9/2001 Fujimoto et al. ............. 382/225
2003/0113029 A1 * 6/2003 McLaughlin ................. 382/244
2004/0001544 A1 * 1/2004 Mehrotra ................... 375/240.1
2005/0010870 A1 * 1/2005 Gu et al. ....................... 715/540
2005/0111835 A1 * 5/2005 Friel et al. ..................... 386/111
2006/0233258 A1 * 10/2006 Holcomb ................. 375/240.21
2006/0282465 A1 * 12/2006 Sharma ...................... 707/104.1
2009/0248724 A1 * 10/2009 Bhattacharjee et al. ...... 707/101

OTHER PUBLICATIONS

Sung Deuk Kim and Jong Beom Ra, An efficient Motion Vector Coding Scheme Based on Minimum Bitrate Prediction, 1999, pp. 1117-11120.*
Baker et al., Compressing Diffferences of Executable Code, 1999, pp. 1-10.*

* cited by examiner

Primary Examiner — Andrew Goldberg (57) ABSTRACT

Systems and methods for information compression. In a first method embodiment, a computer implemented method for compressing information includes finding a closest match entry of a dictionary to a data block, the dictionary stored in computer usable media. A logical exclusive OR combination of the closest match entry and the data block is performed to form a spatial difference vector identifying locations wherein the data block differs from the closest match entry. An information difference vector comprising differences between the data block and the closest match entry is formed. A compressed data block comprising the spatial difference vector, the information difference vector and a reference to the closest match entry is produced. The compressed data block is characterized as being smaller than the data block.

7 Claims, 9 Drawing Sheets

| Null |
| --- |
| *released* |
| Verification Byte(s) |
| Time (last accessed) |
| Times accessed |

720

| Null |
| --- |
| *remaining* |
| Verification Byte(s) |
| Time (last accessed) |
| Times accessed |

730

| Null |
| --- |
| *convention* |
| *delegates* |
| Verification Byte(s) |
| Time (last accessed) |
| Times accessed |

SYSTEMS AND METHODS FOR INFORMATION COMPRESSION

RELATED APPLICATIONS

This Application claims priority to U.S. Provisional Application 61/054,632, filed May 20, 2008, entitled "System and Method for Executing Pattern Matching" to Mustafa, which is hereby incorporated herein by reference in its entirety.

This Application is a Continuation in Part of commonly owned, co-pending U.S. patent application Ser. No. 12/183,722, filed Jul. 31, 2008, entitled "Diversity String Based Pattern Matching" to Mustafa, which is hereby incorporated herein by reference in its entirety, which in turn claims priority to U.S. Provisional Application 61/054,632.

FIELD OF INVENTION

The present invention relates to systems and methods of information compression.

BACKGROUND OF THE INVENTION

The amount of digital information transferred, whether via communication channels, e.g., via the internet or television broadcast, or via computer usable media, e.g., digital versatile discs (DVD), appears to be growing without apparent bound. Compressing such information has at least the dual advantages of enabling more content to be distributed over existing distribution channels as well as providing an apparent transmission speed increase.

While there are myriad conventional systems and methods for compressing information, there is an on-going need for improved systems and methods for compressing information.

SUMMARY OF THE INVENTION

Therefore, a need exists for systems and methods of information compression. A need also exists for systems and methods of information compression with increased compression levels over the conventional art, which also satisfies the above need. An additional need also exists for systems and methods of information compression than encode compressed information utilizing positional differences with respect to reference information, which also satisfies the above needs. A further need exists for systems and methods of information compression that are compatible and complementary with existing systems and methods of conveying digital information from one system to another. Embodiments in accordance with the present invention provide for these needs.

Accordingly, systems and methods for information compression are disclosed. In a first method embodiment, a computer implemented method for compressing information includes finding a closest match entry of a dictionary to a data block, the dictionary stored in computer usable media. A logical exclusive OR combination of the closest match entry and the data block is performed to form a spatial difference vector identifying locations wherein the data block differs from the closest match entry. An information difference vector comprising differences between the data block and the closest match entry is formed. A compressed data block comprising the spatial difference vector, the information difference vector and a reference to the closest match entry is produced. The compressed data block is characterized as being smaller than the data block.

In an alternative method embodiment, a computer implemented method for decompressing a compressed dataset comprises accessing a compressed dataset at a compression processor. The compressed dataset corresponds to an uncompressed dataset. The compressed dataset includes an information difference vector, wherein the information difference vector comprises differences between the uncompressed dataset and a reference dataset available at the compression processor, and a spatial difference vector, wherein the spatial difference vector identifies the location in the uncompressed dataset for elements of the information difference vector. At the compression processor, the uncompressed dataset is recreated from the compressed dataset. Optionally, the uncompressed dataset may be sent to a system for converting the uncompressed dataset to a human usable form.

In yet another embodiment, a computer implemented method for information compression comprises comparing a present dataset for compression to more than one previous datasets to determine a closest match between the dataset for compression and one of the more than one previous datasets. The closest match previous dataset is utilized as a reference for compression of the present dataset.

BRIEF DESCRIPTION OF THE DRAWINGS

These and other aspects and features of the present invention will become apparent to those of ordinary skill in the art upon review of the following description of specific embodiments of the invention in conjunction with the accompanying figures, wherein.

DETAILED DESCRIPTION

Reference will now be made in detail to various embodiments of the invention, examples of which are illustrated in the accompanying drawings. While the invention will be described in conjunction with these embodiments, it is understood that they are not intended to limit the invention to these embodiments. On the contrary, the invention is intended to cover alternatives, modifications and equivalents, which may be included within the spirit and scope of the invention as defined by the appended claims. Furthermore, in the following detailed description of the invention, numerous specific details are set forth in order to provide a thorough understanding of the invention. However, it will be recognized by one of ordinary skill in the art that the invention may be practiced without these specific details. In other instances, well known methods, procedures, components, and circuits have not been described in detail as not to unnecessarily obscure aspects of the invention.

Notation and Nomenclature

Figure 2:
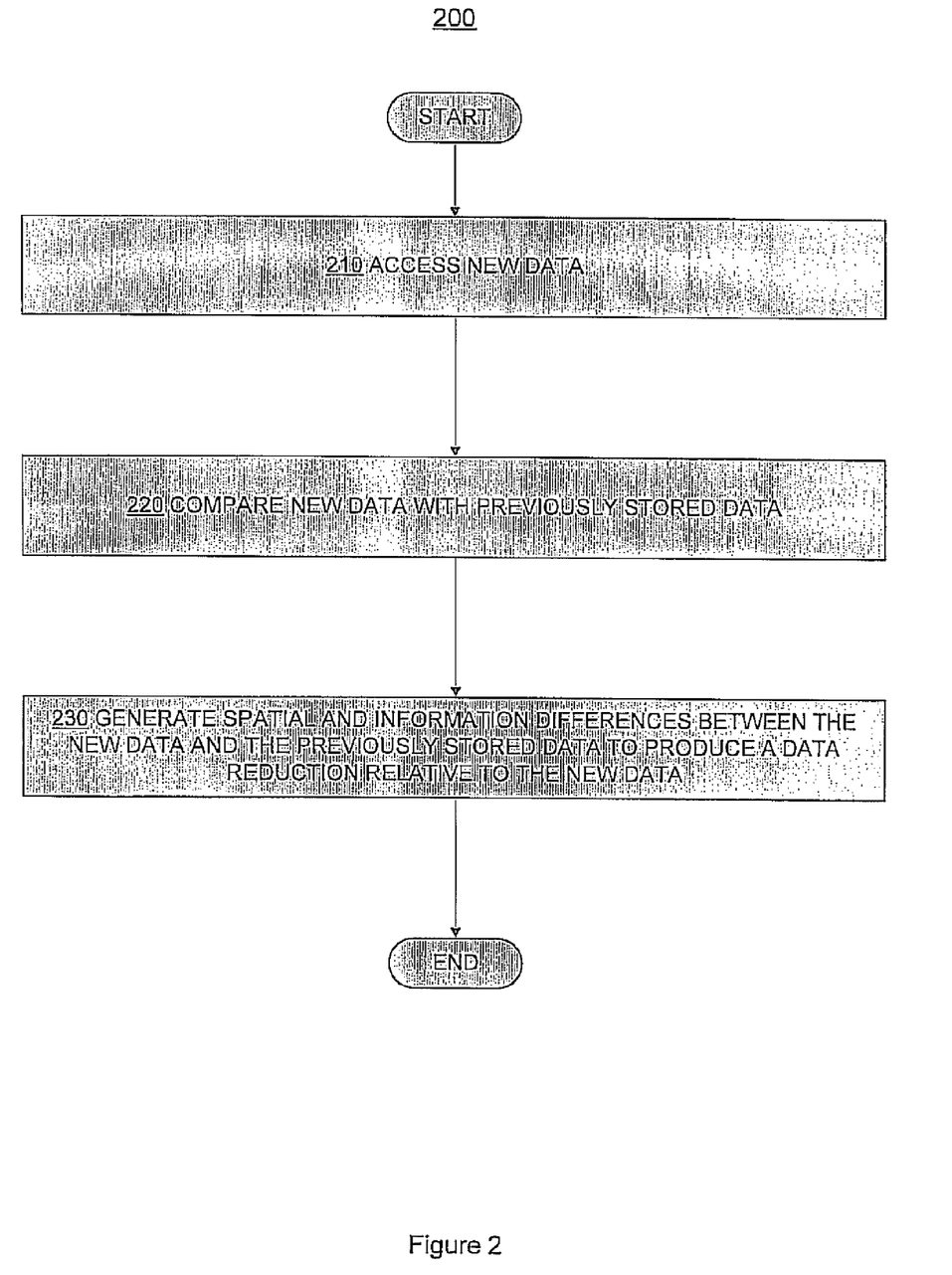
FIG. 2 illustrates a method for compressing information, in accordance with embodiments of the present invention.
Figure 4:
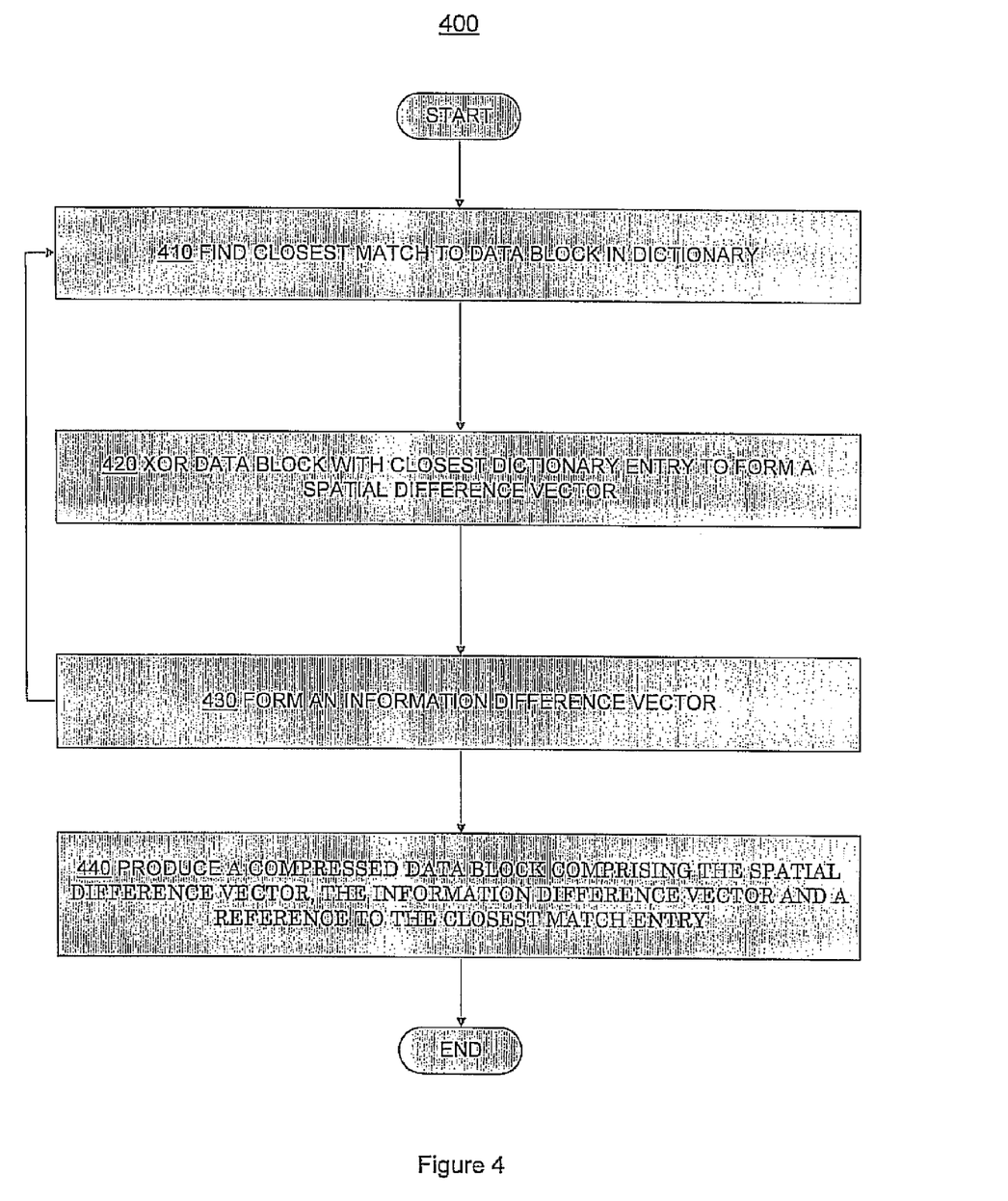
FIG. 4 illustrates a method for compressing information, in accordance with embodiments of the present invention.
Figure 9:
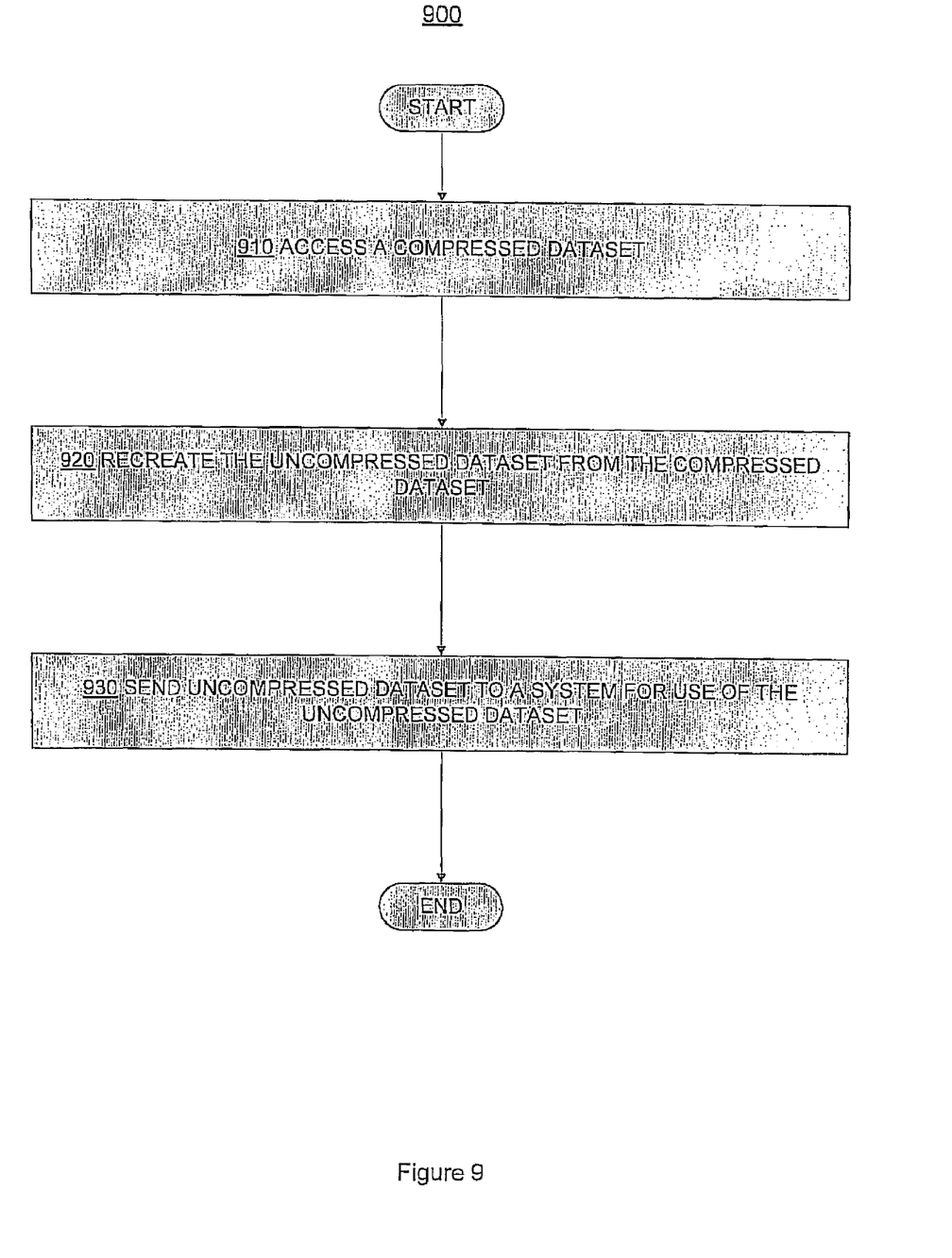
FIG. 9 illustrates a method for decompressing compressed information, in accordance with embodiments of the present invention.

Some portions of the detailed descriptions that follow (e.g., methods 200, 400 and 900) are presented in terms of procedures, steps, logic blocks, processing, and other symbolic representations of operations on data bits that can be performed on computer memory. Such computer memory is functionally coupled to a processor. These descriptions and representations are the means used by those skilled in the data processing arts to most effectively convey the substance of their work to others skilled in the art. A procedure, computer executed step, logic block, process, etc., is here, and generally, conceived to be a self-consistent sequence of steps or instructions leading to a desired result. The steps are those requiring physical manipulations of physical quantities. Usually, though not necessarily, these quantities take the form of electrical or magnetic signals capable of being stored, transferred, combined, compared, and otherwise manipulated in a computer system. Such quantities may be represented in a wide variety of computer usable media, including, for example, computer memory, e.g., RAM or ROM, removable memory, e.g., flash memory, bubble memory, optical storage, e.g., CD or DVD, magneto-optical storage, magnetic storage, e.g., drum, hard drive, diskette or tape, paper tape, punch cards and the like. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise as apparent from the following discussions, it is appreciated that throughout the present invention, discussions utilizing terms such as "finding" or "performing" or "forming" or "producing" of "repeating" or "XOR-ing" or "accessing" or "recreating" or "sending" or "comparing" or "utilizing" or "measuring" or "determining" or "analyzing" or "applying" or "grounding" or "comparing" or "sending" or "commanding" or "storing" or "computing" or "testing" or "calculating" or "measuring" or "adjusting" or the like, refer to the action and processes of a computer system, or similar electronic computing device" that manipulates and transforms data represented as physical (electronic) quantities within the computer system's registers and memories into other data similarly represented as physical quantities within the computer system memories or registers or other such information storage, transmission or display devices.

Systems and Methods for Information Compression

Figure 1:
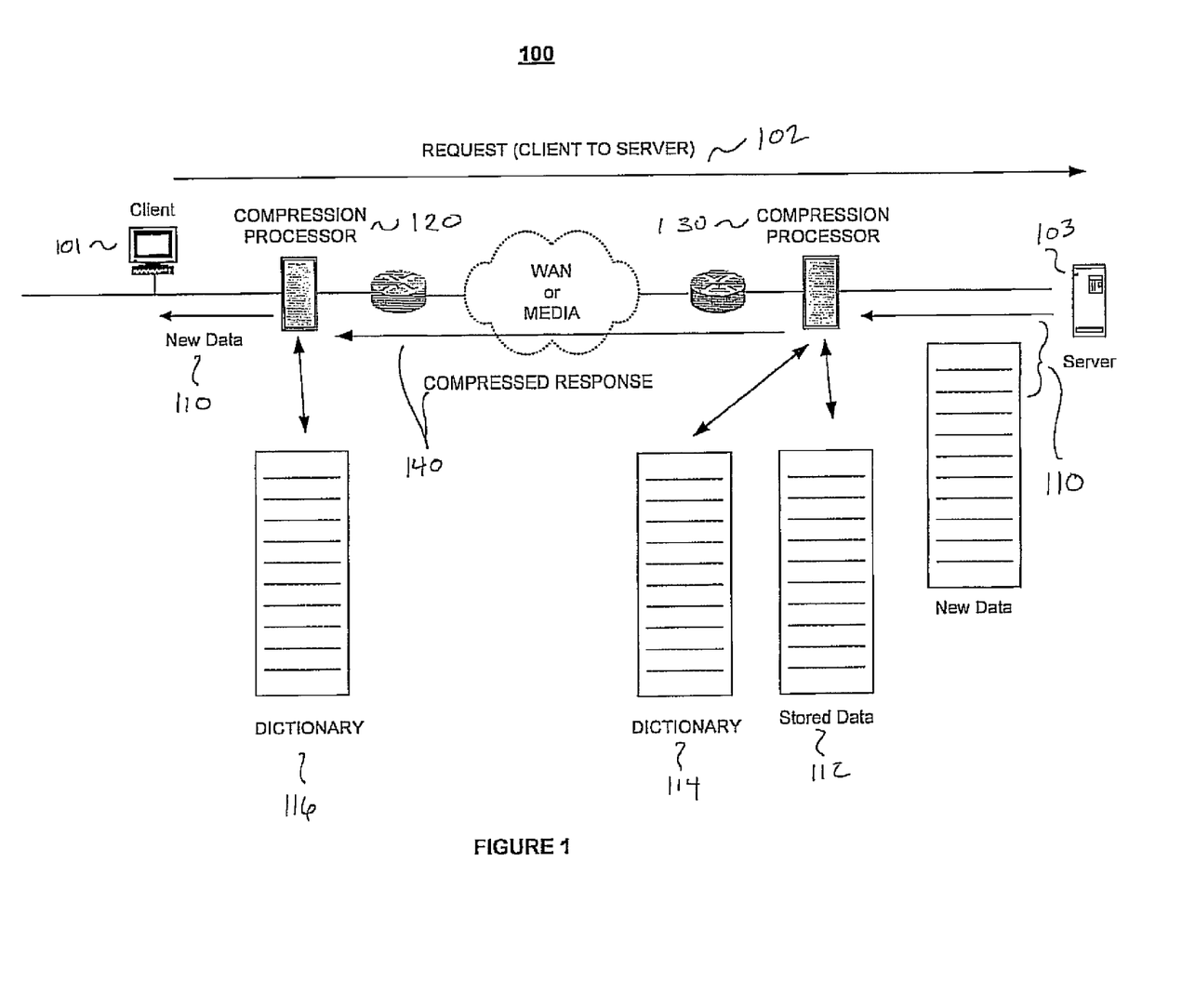
FIG. 1 illustrates a system data flow diagram for an information compression system, in accordance with embodiments of the present invention.

FIG. 1 illustrates a system data flow diagram 100 for an information compression system, in accordance with embodiments of the present invention. In system data flow diagram 100, a client 101 generates an information request 102 to a server 103. The client 101 is communicatively coupled to the server 103 via compression processors 120 and 130. Any suitable communication may be used to couple information processor 120 to information processor 130, for example, the internet or broadcast television. It is to be appreciated that embodiments in accordance with the present invention are well suited to compressed data transfer via a computer usable storage media, e.g., Compact Disc (CD) or Digital Versatile Disc (DVD). As will be further discussed below, compression processors 120, 130 monitor, may intercept and/or interject data traffic between client 101 and server 103, transparent to client 101 and server 103, in order to increase effective data transmission between client 101 and server 103, via novel data compression techniques.

In one embodiment, responsive to information request 102, server 103 generates new data 110. New data 110 is sent toward client 101 from server 103. However, new data 110 is intercepted by compression processor 130. Compression processor 130 compares new data 110 with stored data 112 and dictionary 114 to create a compressed response 140. Compressed response 140 is sent from compression processor 130 to compression processor 120.

Compression processor 120 receives compressed response 140. In conjunction with references to dictionary 116, compression processor 120 is able to reconstruct new data 110, which is forwarded to client 101, as though it had been sent from server 103.

In accordance with another embodiment of the present invention, compressed information 140 may be pushed to client 101 without an information request, e.g., without request 102. Such an embodiment may be useful, for example, in one-way communication systems, e.g., television broadcast, or in playback systems, e.g., playback of prerecorded media, e.g., music or video.

FIG. 2 illustrates a method 200 for compressing information, in accordance with embodiments of the present invention. In 210, new data, e.g., new data 110 of FIG. 1, is accessed by a compression processor, e.g., compression processor 130 of FIG. 1. In 220, the new data is compared with previously stored data, e.g., stored data 112 of FIG. 1. The previously stored data may be an immediately prior, in time or storage location, block of data, e.g., a previously transmitted frame, although that is not required.

Figure 3:
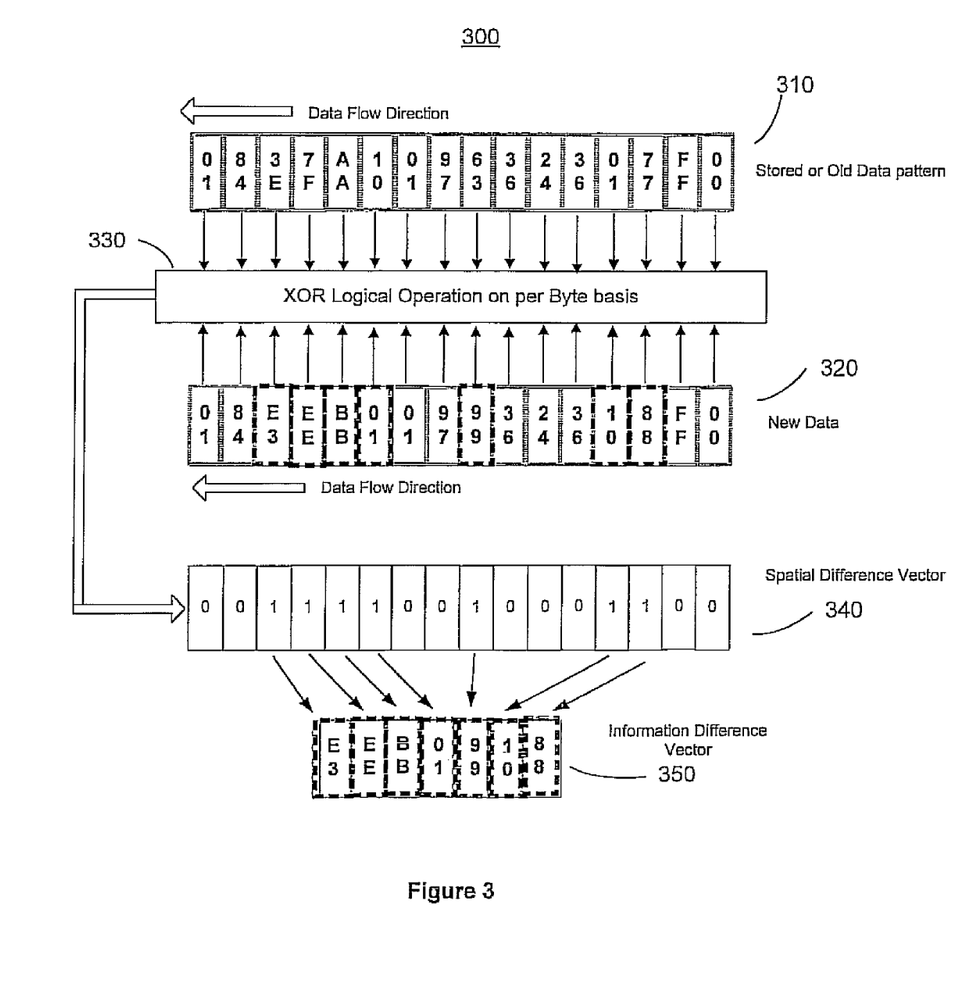
FIG. 3 illustrates an exemplary XOR comparison of new data with previously stored data, in accordance with embodiments of the present invention.

In accordance with embodiments of the present invention, the comparison 220 may be performed via a logical XOR operation on a per-byte basis. FIG. 3 illustrates an exemplary XOR comparison 300 of new data with previously stored data, in accordance with embodiments of the present invention.

In exemplary XOR comparison 300, stored data 310 is XORed 330 with new data 320 to produce a spatial difference vector 340. The data is typically compared on a byte by byte basis, e.g., one byte (e.g., 8 bits) of stored data 310 is compared to one byte of new data 320, producing a single bit in spatial difference vector 340. Embodiments in accordance with the present invention are well suited to other comparison sizes, e.g., bit by bit, or larger block sizes. XOR comparison 330 may be performed by software, by internal logic operations of a processor, or by specialized comparison hardware, in accordance with embodiments of the present invention.

The result of the comparison 330, e.g., spatial difference vector 340, identifies byte (or blocks or other units) locations that differ between the new data and the previously stored data. The actual byte values that differ form an information difference vector 350. In general, a spatial difference vector identifies which bytes (or other data grouping units) are different, whereas an information difference vector identifies the value of the different bytes.

Returning now to FIG. 2, in 230 spatial and information differences between the new data and the previously stored data are generated, producing a data reduction relative to the new data. In this novel manner, data transmission and/or data storage requirements may be reduced.

In accordance with embodiments of the present invention, additional compression and/or decreased transmission requirements may result from further processing of the previously described spatial and information difference vectors.

FIG. 4 illustrates a method 400 for compressing information, in accordance with embodiments of the present invention. In 410 a block of data is searched against a dictionary, e.g., dictionary 114 of FIG. 1, to determine a closest match between the block and a dictionary entry. The search may utilize an XOR mechanism, similar to that described with respect to FIG. 3, to determine the closest match, in accordance with embodiments of the present invention. For example, the block may be XOR-ed with a dictionary entry to determine a number of bytes that differ between the block and the dictionary entry.

In 420, in response to the determining of a closest match among dictionary entries, the block is XOR-ed with the closest matching dictionary entry, forming a spatial difference vector identifying locations at which the data block differs from the closest match entry. In 430, an information difference vector is formed comprising differences between the data block and the closest match entry.

In 440, a compressed data block is produced comprising the spatial difference vector, the information difference vector and a reference to the closest match entry. The compressed data block is characterized as being smaller than the data block.

In accordance with embodiments of the present invention, the present block of information may be raw or uncompressed data. The method 400 may produce a significant data reduction in this embodiment. It is to be appreciated that the method 400 is operable over any type of data, including text, media, e.g., music and/or video, program code and the like.

For example, for a data stream comprising video frames, a dictionary may comprise a plurality of previous frames. It is appreciated that modern computer systems may comprise very large amounts of memory capable of storing a great many video frames. In accordance with embodiments of the present invention, a new video frame may be compared against a great number of prior video frames, in order to find a closest match.

In accordance with embodiments of the present invention, the block of data used in either method 200 (FIG. 2) or method 400 may comprise previously compressed information. For example, with reference once again to FIG. 3, new (uncompressed) data 320 may be processed with stored data 310 to produced a first spatial difference vector 340 and a first information difference vector 350, in accordance with method 200. Subsequently, first spatial difference vector 340 and/or first information difference vector 350 may be processed in view of a dictionary, e.g., dictionary 114 (FIG. 1), according to method 400.

Continuing the example, first information difference vector 350 is XOR-ed with the closest matching dictionary entry, producing a second spatial difference vector and a second information difference vector. In general, the novel dictionary based compression may produce greater compression than other techniques that rely on a fixed relationship, e.g., time or storage location, between comparison entities.

As discussed above, the methods 200 and/or 400 may be utilized together and/or recursively, in accordance with embodiments of the present invention. In a recursive embodiment, information may be compressed multiple times. Termination criteria, e.g., a predetermined number of compression actions and/or a measure of decreasing compression, may be used to determine when to stop recursive compression.

As previously described, embodiments in accordance with the present invention may benefit from maintaining a dictionary, e.g., dictionary 114 (FIG. 1). In general, the dictionary stores previous data sets. However, the dictionary is not limited to storing data that has been generated by server 100 (FIG. 1). Rather, the dictionary is built and maintained by compression processor 130 (FIG. 1) so as to be of increasing benefit to increased compression.

Figure 5:
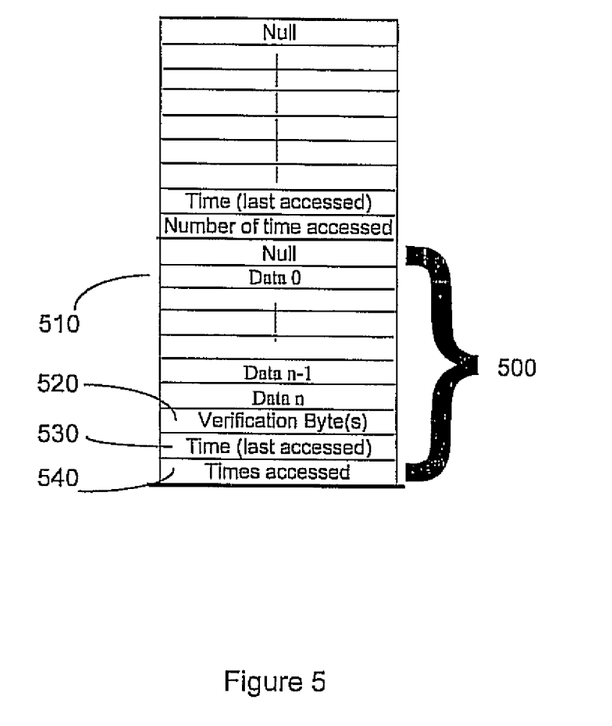
FIG. 5 illustrates an exemplary dictionary entry stored in computer usable memory, in accordance with embodiments of the present invention.

For example, in accordance with embodiments of the present invention, a dictionary may comprise entries including previous uncompressed data, compressed data or pointers to other dictionary entries. FIG. 5 illustrates an exemplary dictionary entry 500 stored in computer usable memory, in accordance with embodiments of the present invention.

Dictionary entry 500 may be fixed length or variable length. Dictionary entry 500 comprises a data section 510. As previously described, data section 510 may comprise a variety of data types, including, for example, uncompressed data, compressed data or pointers to other dictionary entries. Dictionary entry 500 also comprises a plurality of verification bytes 520, a time of last access field 530 and a count of times accessed 540.

Verification bytes 520 identify a valid dictionary entry, and may comprise, for example, a checksum or a cyclic redundancy check (CRC). Verification bytes 520 may also comprise a size indication for variable size entries. The time of last access field 530 and count of times accessed field 540 are utilized to manage dictionary entries. For example, dictionary entries may become "stale" if not used frequently. The count of times accessed field 540 counts the number of times a particular entry 500 has been the closest matching entry. In general, a higher value in count of times accessed field 540 indicates a more valuable entry, e.g., it has been utilized frequently for compression.

In accordance with embodiments of the present invention, a dictionary comprising a plurality of entries, e.g., entry 500, improves the efficiency and compression ratio of compressed information, in comparison with the conventional art. For example, a dictionary serves as an improved history of previous data. In accordance with embodiments of the present invention, the dictionary is maintained such that infrequently used or "old" entries expire. For example, an independent dictionary maintenance process may parse dictionary entries, removing infrequently used or "old" entries. Entries may be removed after a predetermined period of unuse, or the oldest entries may be removed, for example. Newer and/or more frequently used entries are accumulated.

In this novel manner, the content of the dictionary becomes more optimal over time, increasing the "closeness" of the dictionary entries to the comparison data, e.g., new data 320 of FIG. 3. It is to be appreciated that an ideal dictionary entry would be identical to the comparison data. In such a case, a reference to the dictionary entry completely represents the comparison data, e.g., new data 320 of FIG. 3. Such matches enable very high rates of compression. By maintaining and updating the dictionary, there are ever fewer differences between dictionary entries and comparison data, and the incidence of an exact match increases.

In accordance with embodiments of the present invention, the dictionary may be optimized to correspond with the type of data being communicated. For example, human language text has a relatively low information content, and a dictionary of common words and/or phrases, in conjunction with the systems and methods elsewhere described herein, may lead to very high compression rates, e.g., representing multi-word phrases with a reference to a single dictionary entry. Similarly, more optimized dictionaries may be generated based on other types of content, e.g., music, pictures, video, executable software and the like.

Commonly owned, co-pending U.S. patent application Ser. No. 12/183,772, filed Jul. 31, 2008, entitled "Diversity String Based Pattern Matching" to Mustafa, hereby incorporated herein by reference in its entirety, presents novel methods of determining the content of data. Embodiments in accordance with the present invention are compatible, complimentary and well suited to generating and/or selecting dictionaries based on the systems and methods taught in U.S. patent application Ser. No. 12/183,772.

Figure 6:
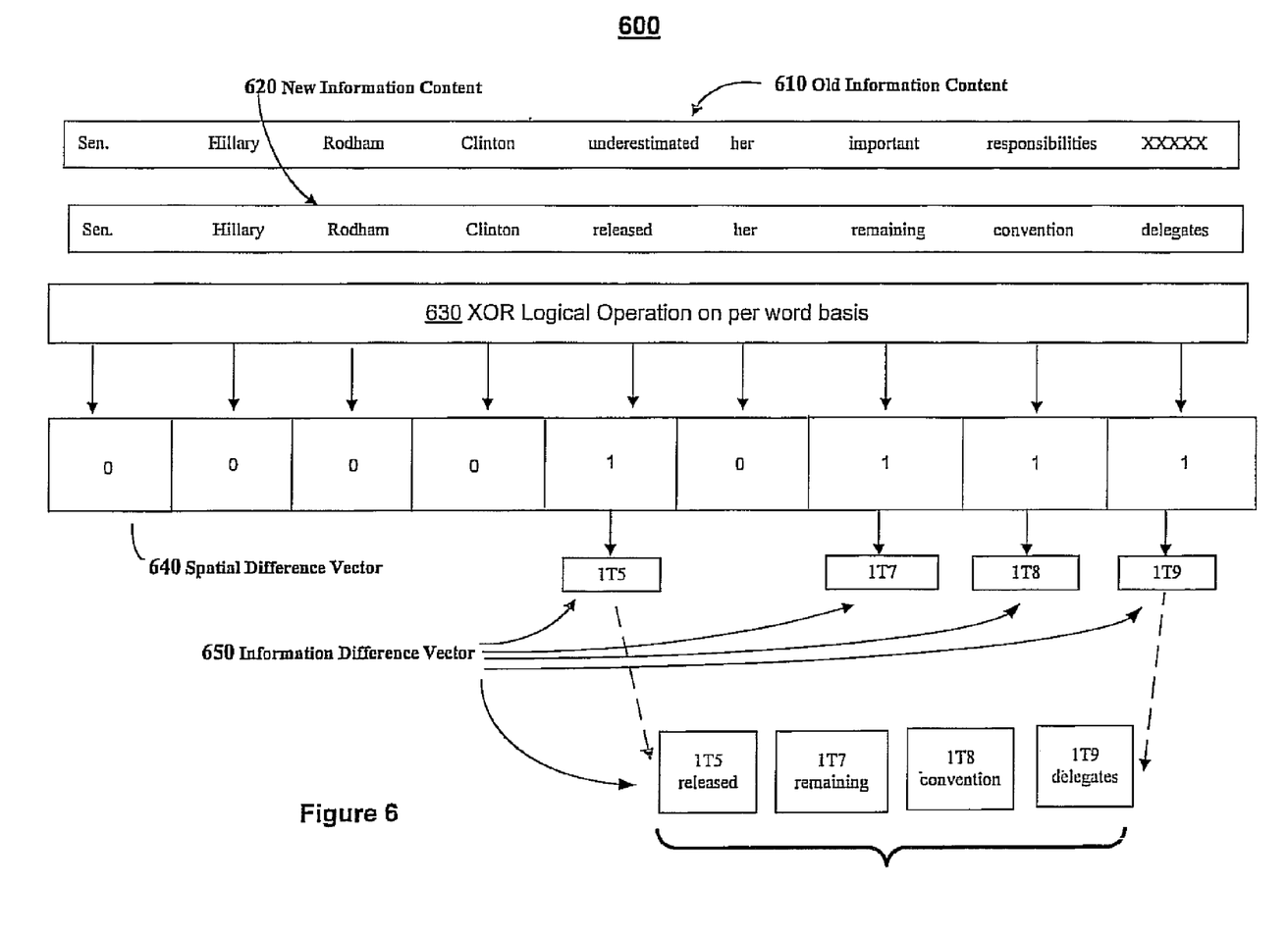
FIG. 6 illustrates a data flow diagram for a first portion of an exemplary compression operation, in accordance with embodiments of the present invention.

FIG. 6 illustrates a data flow diagram 600 for a first portion of an exemplary compression operation, in accordance with embodiments of the present invention. Data flow diagram 600 illustrates a data set 610 comprising eight words (or abbreviations). Data set 610 is "old" data, for example it has been previously transmitted from server 103 to client 101 (FIG. 1). Data set 620 comprises nine words (or abbreviations), and is new data, e.g., it has just been sent from server 103 toward client 101.

Exclusive OR operation 630 identifies word locations in which data set 610 differs from data set 620, producing a spatial difference vector 640, in bits. Information difference vector 650 comprises the word differences between data set 610 and data set 620. For example, the word differences between data set 610 and data set 620 comprise "released" in the fifth position, "remaining" in the seventh position, "convention" in the eighth position and "delegates" in the ninth position. It is appreciated that old data set 610, spatial difference vector 640 and information difference vector 650 enable reconstruction of new data set 620. Consequently, in accordance with embodiments of the present invention, it is only necessary to transmit spatial difference vector 640 and information difference vector 650 from compression processor 130 to compression processor 120 (FIG. 1) in order for compression processor 120 to fully and accurately reconstruct new data set 620, for forwarding to client 101.

Figure 7:
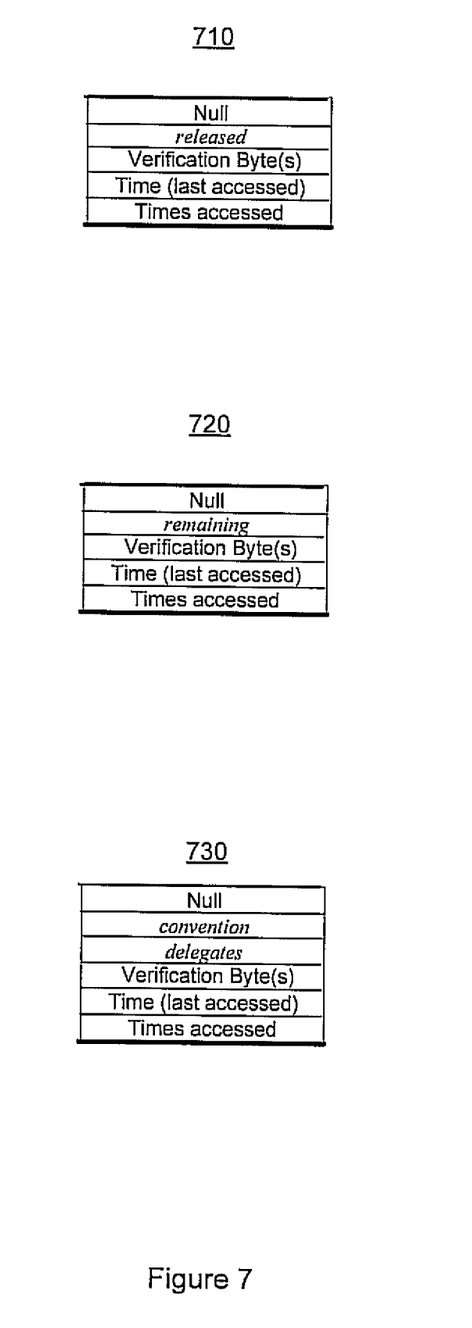
FIG. 7 illustrates three exemplary dictionary entries, in accordance with embodiments of the present invention.

While the compression described above with respect to FIG. 6 may be beneficial, in accordance with embodiment of the present invention, higher and more desirable levels of compression may be obtained with reference to a dictionary, as previously described. FIG. 7 illustrates three exemplary dictionary entries, in accordance with embodiments of the present invention.

Referring to FIGS. 4, 6 and 7, a dictionary is searched, per 410, for a closest match to information difference vector 650. Dictionary entry 730 matches two words, "convention" and "delegates." Dictionary entries 710 and 720 each match one word, "released" and "remaining," respectively. At this point the new data 620 may be reconstructed from old data set 610, spatial difference vector 640 and dictionary entries 710, 720 and 730. Consequently, in accordance with embodiments of the present invention, it is only necessary to transmit spatial difference vector 640 and references to dictionary entries 710, 720 and 730 from compression processor 130 to compression processor 120 (FIG. 1) in order for compression processor 120 to fully and accurately reconstruct new data set 620, for forwarding to client 101.

Figure 8:
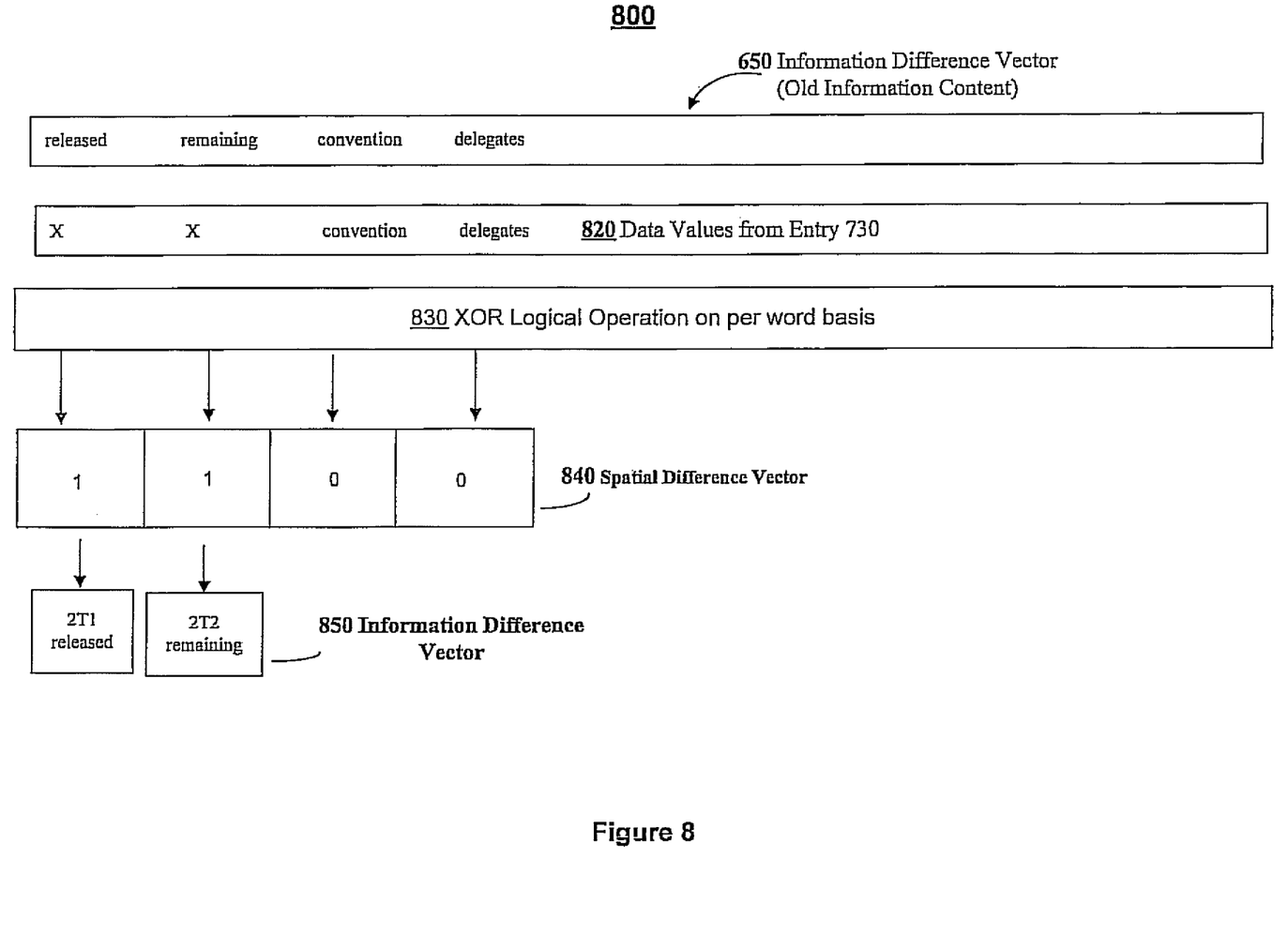
FIG. 8 illustrates a recursive combining, in accordance with embodiments of the present invention.

As discussed previously, method 400 may be employed recursively. For example, information difference vector 650 may be XOR-ed with the data values of dictionary entry 730 to produce a second information difference vector. FIG. 8 illustrates a recursive combining 800, in accordance with embodiments of the present invention.

In recursive combining 800, the information difference vector 650 (FIG. 6), which was produced as a result of the compression described with respect to FIG. 6, is combined with the data values 820 from dictionary entry 730 (FIG. 7). The combining produces a spatial difference vector 840 and an information difference vector 850. It is appreciated that both spatial difference vector 840 and information difference vector 850 are smaller, e.g., contain less entries, than the corresponding spatial difference vector 640 and information difference vector 650 resulting from a single compression action.

It is to be appreciated that the new data 620 (FIG. 6) may be reconstructed from old data set 610, spatial difference vector 840, information difference vector 850 and dictionary entry 730 (FIG. 7). Consequently, in accordance with embodiments of the present invention, it is only necessary to transmit spatial difference vector 840, information difference vector 850 and a reference to dictionary entry 730 from compression processor 130 to compression processor 120 (FIG. 1) in order for compression processor 120 to fully and accurately reconstruct new data set 620, for forwarding to client 101. In this novel manner, recursive compression may beneficially increase the level of compression, advantageously decreasing the amount of data necessary to be transmitted or stored in order to convey the desired message.

In general, after every search of a dictionary, a new dictionary entry may be created. For example, a threshold value for a number of data groups, e.g., human language words, bytes, etc., may be utilized as part of a criteria to determine whether to create a new dictionary. For example, if no two word matches are found, then a dictionary entry comprising two words from the information difference vector may be created. Further, multiple dictionary entries may be created for other two word combinations in the information difference vector. Higher order, e.g., three or more, dictionary entries may also be created, based on such higher order word combinations from an information difference vector.

As previously described, dictionary entries are dynamic. They may be created according to a computed need, and they may be removed or destroyed based on lack of use or age. Dictionary entries are generally created by compression processor 130, and are not generally created by compression processor 120, unless, for example, generally equal levels of traffic flow in both directions. In such a case, the transmit/receive and compression/decompression roles of compression processors 130 and 120 may be exchanged. When new dictionary entries are created, such creation should be signaled from the creator, e.g., compression processor 130, to the other compression processor(s), e.g., compression processor 120. It is appreciated that it is generally not necessary to signal removal of a directory entry, as similar dictionary entry maintenance processes on all compression processors should remove directory entries at about the same time.

FIG. 9 illustrates a method 900 for decompressing compressed information, in accordance with embodiments of the present invention. In 910, a compressed dataset is accessed. The compressed dataset may be received via a communication channel, e.g., over the internet. Alternatively, the compressed dataset may be accessed from a computer usable storage media, for example, a compact disc (CD), a flash ROM, e.g., a USB drive or a flash media card, e.g., a Secure Digital card, a digital versatile disc (DVD) and the like.

In accordance with embodiments of the present invention, the compressed dataset corresponds to an uncompressed dataset. The uncompressed dataset comprises an information difference vector. The spatial information vector identifies groups of data, e.g., bytes or a representation of words in human readable text, that differ between the uncompressed dataset and a reference dataset. The reference dataset is available at a system performing the decompressing. The uncompressed dataset further comprises a spatial difference vector. The spatial difference vector identifies the location in the uncompressed dataset where the groups of data (information difference vector) belong. The compressed dataset may also comprise a reference to a dictionary entry. A dictionary comprising the dictionary entry is available at a system performing the decompressing.

In 920, the uncompressed dataset is recreated from the compressed dataset. In optional 930, the uncompressed dataset is sent to a system for converting the uncompressed dataset to a human usable form. For example, the system may be a computer capable of displaying hypertext transfer protocol (HTTP) messages to a user, e.g., via a display screen. Alternatively, the system may be capable of playback of digital media content, e.g., digital music and/or video. The playback system may be physically integrated with the decompression system, although this is not required.

Embodiments in accordance with the present invention provide for systems and methods of information compression. Embodiments in accordance with the present invention also provide for systems and methods of information compression with increased compression levels over the conventional art, which also satisfies the above need. Additional embodiments in accordance with the present invention provide for systems and methods of information compression than encode compressed information utilizing positional differences with respect to reference information, which also satisfies the above needs. Further embodiments in accordance with the present invention provide for systems and methods of information compression that are compatible and complementary with existing systems and methods of conveying digital information from one system to another.

Various embodiments of the invention are thus described. While the present invention has been described in particular embodiments, it should be appreciated that the invention should not be construed as limited by such embodiments, but rather construed according to the below claims.

What is claimed is:

1. A non-transitory computer-readable medium having computer-readable program code embodied therein for causing a computer system to perform a method for compressing information, the method comprising:

finding a closest match entry in a dictionary to an incoming data block, the data block containing portions of data, each portion larger than one bit, said dictionary stored in computer usable media within said non-transitory computer-readable medium, wherein said dictionary comprises a plurality of entries for matching with said data block;

performing a logical exclusive OR on each portion of said closest match entry and said data block to form a spatial difference vector identifying locations where said data block differs from said closest match entry, the spatial difference vector contains corresponding bit locations wherein each bit location contains a one bit value to indicate if said portion of data differs or not;

forming an information difference vector only comprising differences between said data block and said closest match entry; and producing a compressed data block comprising said spatial different vector, said information difference vector and a reference to said closest match entry, wherein said compressed data block is characterized as being smaller than said data block; and wherein the dictionary comprises uncompressed data, compressed data and pointers to other dictionary entries, wherein an entry in the dictionary comprises verification bytes to identify a valid dictionary entry, wherein an independent dictionary maintenance process removes the oldest entries in the dictionary.

2. The computer-readable medium of claim 1 further comprising repeating said finding, said performing and said forming with said information difference vector serving as a new said data block.

3. The computer-readable medium of claim 1 wherein said logical exclusive OR combination compares groups of data larger than one bit and produces one bit of output for each of said groups compared.

4. The computer-readable medium of claim 3 wherein said groups comprise bytes of data.

5. The computer-readable medium of claim 3 wherein said groups comprise data sets corresponding to words of human readable text.

6. The computer-readable medium of claim 5 wherein said groups have variable length corresponding to the length of said words of human readable text.

7. The computer-readable medium of claim 1 wherein said data block corresponds to a frame of video data.

\* \* \* \* \*